(12) United States Patent
Howard

(10) Patent No.: US 6,387,904 B2
(45) Date of Patent: May 14, 2002

(54) METHOD OF TREATING GLAUCOMA AND ISCHEMIC RETINOPATHY

(75) Inventor: Harry R. Howard, Bristol, CT (US)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 09/314,792

(22) Filed: May 18, 1999

Related U.S. Application Data

(60) Provisional application No. 60/085,867, filed on May 18, 1998, and provisional application No. 60/086,745, filed on May 26, 1998.

(51) Int. Cl.⁷ .............................................. A61K 31/50
(52) U.S. Cl. ............... 514/252.1; 514/247; 514/252.12; 514/252.13; 514/255.05
(58) Field of Search .................. 514/247, 252.1, 514/253, 252.12, 252.13, 255.05

(56) References Cited

U.S. PATENT DOCUMENTS 4,831,031 A * 5/1989 Lowe, III et al. ........... 514/254
5,196,434 A * 3/1993 Taverne et al. ............. 514/278

* cited by examiner

*Primary Examiner*—Zohreh Fay
*Assistant Examiner*—C. Delacroix-Muirheid
(74) *Attorney, Agent, or Firm*—Peter C. Richardson; Paul H. Ginsburg

(57) ABSTRACT

A method for treating glaucoma and ischemic retinopathy in a mammal, comprising administering to said mammal a therapeutically effective amount of a compound of the formula

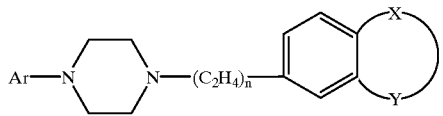

(I)

or a pharmaceutically acceptable acid addition salt thereof, wherein n, X, Y and Ar are as defined in the specification.

10 Claims, No Drawings

METHOD OF TREATING GLAUCOMA AND ISCHEMIC RETINOPATHY

This application claims priority under 35 U.S.C. § 119(e) from U.S. Provisional Application Serial No. 60/085,867, filed May 18, 1998 and from U.S. Provisional Application Serial No. 60/086,745, filed May 26, 1998.

BACKGROUND OF THE INVENTION

The present invention relates to the use of piperazinyl-heterocyclic compounds of the formula I, as defined below, for the treatment of glaucoma and ischemic retinopathy.

The piperazinyl-heterocyclic compounds of formula I and their utility for the treatment of psychotic disorders, including schizophrenia, are referred to in U.S. Pat. Nos. 4,831,031 and 4,883,795, which issued, respectively, on May 16, 1989 and Nov. 28, 1989. The ulitity of such compounds for the treatment of obsessive-compulsive disorder and Tourette's syndrome is referred to in U.S. Provisional Application 60/057,987, which was filed on Sep. 5, 1997. The utility of such compounds for the treatment of certain psychiatric disorders that have as symptoms behavioral disturbances (e.g., anxiety, bipolar disorder, major depressive disorder, autistic disorder, conduct disorder, dementias including dementias associated with Alzheimer's disease, and drug induced and neurodegeneration based dyskinesias is referred to in U.S. Provisional Application 60/068,069, which was filed on Dec. 18, 1997. All of the foregoing patents and patent applications are assigned in common with the present application.

Current treatments for glaucoma include the use of beta-adrenergic antagonists such as timolol and betaxolol, which, like the compounds administered in the methods of this invention (i.e., compounds of the formula I, as defined below), are effective in reducing intraocular pressure. The compounds of formula I, however, do not exhibit beta-adrenergic blocking activity and thus do not have associated with them the negative cardiac side effects that are associated with beta-adrenergic blockers (e., systemic absorption leading to slowing of the heart).

Methods of preparing the novel compounds of the formula I and their pharmaceutically acceptable salts are referred to in each of the following: U.S. Pat. Nos. 4,831,031 and 4,883,795, referred to above, and in U.S. Pat. Nos. 5,206,366 and 5,338,846, which were issued, respectively, on Apr. 27, 1993 and Aug. 16, 1994. All of the foregoing patents are assigned in common with the present application and incorporated herein by reference in their entireties.

SUMMARY OF THE INVENTION

The present invention also relates to a method of treating a disorder or condition that can be treated by decreasing intraocular pressure in a mammal, including a human, comprising administering to said mammal a therapeutically effective amount of a compound of the formula

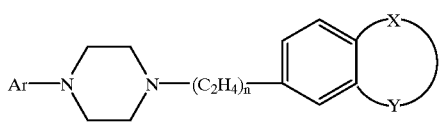

(I)

or a pharmaceutically acceptable acid addition salt thereof, wherein

Ar is benzoisothiazolyl or an oxide or dioxide thereof each optionally substituted by one fluoro, chloro, trifluoromethyl, methoxy, cyano or nitro; naphthyl optionally substituted by fluoro, chloro, trifluoromethyl, methoxy, cyano or nitro; quinolyl; 6-hydroxy-8-quinolyl; isoquinolyl; quinazolyl; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; or phthalazinyl;

n is 1 or 2; and

X and Y together with the phenyl to which they are attached form a cyclic ring system selected from quinolyl; 2-hydroxyquinolyl; benzothiazolyl; 2-aminobenzothiazolyl; benzoisothiazolyl; indazolyl; 2-hydroxyindazolyl; indolyl; oxindolyl optionally substituted by spirocycloalkyl wherein said cycloalkyl moiety contains from 4 to 7 carbon atoms, or by one to three of $(C_1-C_3)$alkyl, or by one of chloro, fluoro or phenyl wherein said phenyl is optionally substituted by one chloro or fluoro; benzoxazolyl; 2-aminobenzoxazolyl; benzoxazolonyl; 2-aminobenzoxazolinyl; benzothiazolonyl; benzoimidazolonyl; and benzotriazolyl.

The present invention also relates to a method for treating glaucoma (e.g., open angle glaucoma, wide angle glaucoma, aphakic glaucoma and secondary glaucoma) or ischemic retinopathy (i.e., ischemic retinal degeneration) in a mammal, including a human, comprising administering to said mammal a therapeutically effective amount of compound of the formula

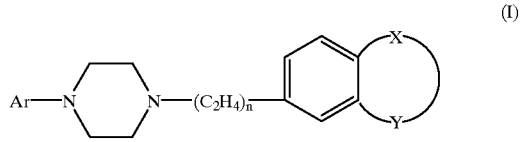

(I)

or a pharmaceutically acceptable acid addition salt thereof, wherein

Ar is benzoisothiazolyl or an oxide or dioxide thereof each optionally substituted by one fluoro, chloro, trifluoromethyl, methoxy, cyano or nitro; naphthyl optionally substituted by fluoro, chloro, trifluoromethyl, methoxy, cyano or nitro; quinolyl; 6-hydroxy-8-quinolyl; isoquinolyl; quinazolyl; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; or phthalazinyl;

n is 1 or 2; and

X and Y together with the phenyl to which they are attached form a cyclic ring system selected from quinolyl; 2-hydroxyquinolyl; benzothiazolyl; 2-aminobenzothiazolyl; benzoisothiazolyl; indazolyl; 2-hydroxyindazolyl; indolyl; oxindolyl optionally substituted by spirocycloalkyl wherein said cycloalkyl moiety contains from 4 to 7 carbon atoms, or by one to three of $(C_1-C_3)$alkyl, or by one of chloro, fluoro or phenyl wherein said phenyl is optionally substituted by one chloro or fluoro; benzoxazolyl; 2-aminobenzoxazolyl; benzoxazolonyl; 2-aminobenzoxazolinyl; benzothiazolonyl; benzoimidazolonyl; and benzotriazolyl.

This invention also relates to a method of treating a disorder or condition that can be treated by improving blood flow in the retina of a mammal, including a human, comprising administering to said mammal a therapeutically effective amount of a compound of the formula

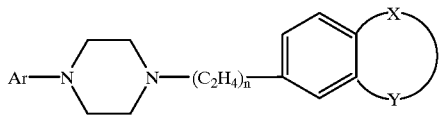

(I)

or a pharmaceutically acceptable acid addition salt thereof, wherein
Ar is benzoisothiazolyl or an oxide or dioxide thereof each optionally substituted by one fluoro, chloro, trifluoromethyl, methoxy, cyano or nitro; naphthyl optionally substituted by fluoro, chloro, trifluoromethyl, methoxy, cyano or nitro; quinolyl; 6-hydroxy-8-quinolyl; isoquinolyl; quinazolyl; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; or phthalazinyl;
n is 1 or 2; and
X and Y together with the phenyl to which they are attached form a cyclic ring system selected from quinolyl; 2-hydroxyquinolyl; benzothiazolyl; 2-aminobenzothiazolyl; benzoisothiazolyl; indazolyl; 2-hydroxyindazolyl; indolyl; oxindolyl optionally substituted by spirocycloalkyl wherein said cycloalkyl moiety contains from 4 to 7 carbon atoms, or by one to three of ($C_1$–$C_3$)alkyl, or by one of chloro, fluoro or phenyl wherein said phenyl is optionally substituted by one chloro or fluoro; benzoxazolyl; 2-aminobenzoxazolyl; benzoxazolonyl; 2-aminobenzoxazolinyl; benzothiazolonyl; benzoimidazolonyl; and benzotriazolyl.

The term "treating", as used herein, refers to reversing, alleviating, inhibiting the progress of, or preventing the disorder or condition to which such term applies, or one or more symptoms of such disorders or condition. The term "treatment", as used herein, refers to the act of treating, as "treating" is defined immediately above.

The term "therapeutically effective amount", as used herein, refers to an amount of a compound of the formula I, or a pharmaceutically acceptable salt thereof, that is effective in treating the disorder or condition for which such compound or salt is being administered.

A preferred embodiment of this invention relates to any of the inventive methods described above wherein the compound of formula I or pharmaceutically acceptable salt is administered is for the treatment of glaucoma.

Another preferred embodiment of this invention relates to any of the inventive methods described above wherein the compound of formula I or pharmaceutically acceptable salt is administered for the treatment of ischemic retinopathy.

Another preferred embodiment of this invention relates to any of the inventive methods described above wherein the compound of formula I or pharmaceutically acceptable salt that is administered is one wherein Ar is benzoisothiazolyl and n is 1.

Another preferred embodiment of this invention relates to any of the inventive methods described above wherein the compound of formula I or pharmaceutically acceptable salt that is administered is one wherein X and Y, together with the phenyl moiety to which they are attached, form an oxindole group that is optionally substituted by chloro, fluoro or phenyl.

Another preferred embodiment of this invention relates to any of the inventive methods described above wherein the compound of formula I or pharmaceutically acceptable salt that is administered is one wherein Ar is naphthyl and n is 1.

Another preferred embodiment of this invention relates to any of the inventive methods described above wherein the compound of formula I or pharmaceutically acceptable salt that is administered is ziprasidone (5-[2-{4-(1,2-benzisothiazol-3-yl)-1-piperazinyl}ethyl]-6-chloro-1,3-dihydro-2H-indole-2-one) or a pharmaceutically acceptable salt thereof.

DETAILED DESCRIPTION OF THE INVENTION

The piperazinyl-heterocyclic compounds of formula I can be prepared by one or more of the synthetic methods described and referred to in U.S. Pat. Nos. 4,831,031; 4,883,795; 5,206,366 and 5,338,846. A preferred method of making such compounds is referred to in U.S. Pat. No. 5,338,846.

The compounds of formula I may be prepared by reacting piperazines of the formula II with compounds of the formula III as follows:

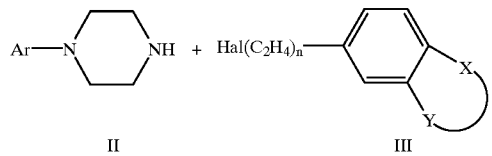

II                              III wherein Hal is fluoro, chloro, bromo or iodo. This coupling reaction is generally conducted in a polar solvent such as a lower alcohol (e.g., ethanol), dimethylformamide or methylisobutylketone in the presence of a weak base such as a tertiary amine base (e.g., triethylamine or diisopropylethylamine). Preferably, the reaction is also carried out in the presence of a catalytic amount of sodium iodide, and in the presence of a neutralizing agent for hydrochloride such as sodium carbonate. This reaction is preferably carried out at the reflux temperature of the solvent.

The piperazine derivatives of formula II may be prepared by methods well known in the art. For example, such compounds can be prepared by reacting an aryl halide of the formula ArHal, wherein Ar is as defined above and Hal is fluoro, chloro, bromo or iodo, with piperazine in a hydrocarbon solvent such as toluene, at a temperature from about room temperature to about the reflux temperature, for about a half hour to about 24 hours. Alternatively, compounds of the formula II may be prepared by heating an amino substituted aryl compound of the formula $ArNH_2$, wherein Ar is as defined above, with a compound of the formula VI

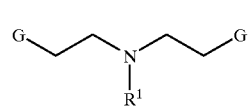

VI wherein G is a leaving group such as chloro, bromo or mesylate and $R^1$ is a group such as benzyl or $COOR^2$ wherein $R^2$ is benzyl or ($C_1$–$C_6$) alkyl, which can be subsequently removed to form the piperizine ring that is attached to the aryl group Ar.

The compounds of formula III may also be prepared by well known methods. For instance, they can be prepared by reacting a haloacetic acid or halobutyric acid, wherein the halogen substituent is fluoro, chloro, bromo or iodo, with a compound of the formula IV as follows:

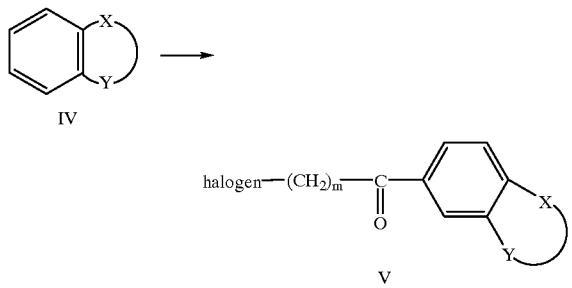

wherein X and Y are as defined above and m is 1 or 3. The resulting compounds of the formula V are then reduced, e.g., with triethylsilane and trifluoroacetic acid in a nitrogen atmosphere, to form compounds of the formula III.

When Ar is the oxide or dioxide of benzoisothiazolyl, the corresponding benzoisothiazolyl compound is oxidized under acid conditions at low temperatures. The acid used is preferably a mixture of sulphuric acid and nitric acid.

Preferably, compounds of the formula I are prepared by reacting a piperazine salt of the formula

wherein Z is fluoro, chloro, bromo, iodo, methanesulfonate, trifluoromethanesulfonate, or trifluoroacetate, and Ar is as defined above, with an alkyl halide containing a compound of the formula

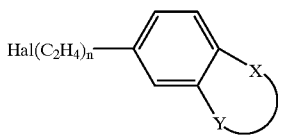

wherein n, X and Y are as defined above and Hal is fluoro, chloro, bromo or iodo, in water with an excess of reagent to neutralize the hydrohalic acid, heating the mixture under conditions which are suitable to effect the coupling of said piperazine salt with said alkyl halide containing compound, and, if desired, preparing the corresponding pharmaceutically acceptable acid addition salt. Preferably, the mixture is heated to about the reflux temperature. Especially preferably, the compound of formula I is reacted with aqueous hydrochloric acid to form a hydrochloride monohydrate.

The pharmaceutically acceptable acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzenesulfonic, and related acids.

Compounds of formula I, and their pharmaceutically acceptable salts (referred to collectively, hereinafter, as "the active compounds of this invention"), can be administered to a human subject either alone, or, preferably, in combination with pharmaceutically-acceptable carriers or diluents, in a pharmaceutical practice. Such compounds can be administered orally or topically (e.g., in the form of eye drops, ointments or lotions). In such topical pharmaceutical dosage forms, the active agent will generally be present in a concentration of about 0.05 to 1.0 weight percent, preferably in a concentration of about 0.12 to about 0.5 weight percent. The weight percent of the active agent will depend on such factors as the solubility of the active component, the dosage contemplated and the precise route of administration.

For oral use, the active compounds of this invention can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added.

When an active compound of this invention is to be used in a human subject to treat glaucoma or icshemic retinopathy, the daily dosage will normally be determined by the prescribing physician. Moreover, the dosage will vary according to the age, weight and response of the individual patient as well as the severity of the patient's symptoms. However, in most instances, an effective amount for treating such disorders will be a daily dosage in the range from about 0.025 mg per day to about 20 mg per day, and preferably from 0.5 mg per day to about 8.0 mg per day, in single or divided doses, orally or topically. In some instances it may be necessary to use dosages outside these limits.

The active compounds of this invention may also be administered in combination with one or more other active agents that are anti-glaucoma agents, either as part of the same pharmaceutical composition or in a separate pharmaceutical composition as part of the same dose regimen. Examples of anti-glaucoma agents that can be used in combination with the active compounds of this invention are beta-adrenergic receptor antagonists such as betaxolol and timolol, and carbonic anhydrase inhibitors such as acetazolamide and dorzolamide.

The receptor binding and neurotransmitter uptake inhibition profile for ziprasidone, 5-(2-(4-(1,2-benzisothiazol-3-yl)piperazinyl)ethyl)-6-chlorooxindole hydrochloride, was described in The Journal of Pharmacology and Experimental Therapeutics, 275, 101–113 (1995), which is incorporated herein by reference in its entirety. A summary of its affinity (pKi) for various receptors in the central nervous system tissue is presented in Table 1.

TABLE 1

| Receptor (Ligand) | pKi |
|---|---|
| DA D1([$^3$H]SCH23390) | 6.28 ± 0.17 (3) |
| DA D2([$^3$H]spiperone) | 8.32 ± 0.04 (6) |
| DA D3([$^3$H]raclopride) | 8.14 ± 0.03 (3) |
| DA D4([$^3$H]spiperone) | 7.49 ± 0.11 (3) |
| 5-HT2A([$^3$H]ketanserin) | 9.38 ± 0.03 (5) |
| 5-HT1A([$^3$H]-8OH-DPAT) | 8.47 ± 0.05 (4) |
| 5-HT2C-([$^3$H]mesulergine) | 8.88 ± 0.05 (6) |
| 5-HT1D-([$^3$H]-5-HT) | 8.69 ± 0.04 (6) |
| Alpha-1 ([$^3$H]prazosin) | 7.98 ± 0.03 (3) |
| Histamine H1 ([$^3$H]mepyramine) | 7.33 ± 0.07 (3) |
| Neurotransmitter Reuptake Blockade: | |
| Norpinephrine | 7.30 ± 0.01 (4) |
| 5-HT | 7.29 ± 0.06 (3) |
| DA | 6.58 ± 0.02 (3) |

Ziprasidone has been found effective for the following indications: psychotic disorders, acute mania, anxiety states, schizophrenia, bipolar disorder, Alzheimer's disease (delusions, delirium), depression and psychotic disorders.

The following examples illustrate methods of preparing various compounds of formula I.

EXAMPLE 1

6-(2-(4-(1-Naphthyl)piperazinyl)ethyl)-benzoxazolone hydrochloride

A. To a 500 ml three-necked round-bottomed flask equipped with mechanical stirrer and nitrogen inlet were added 200 grams of polyphosphoric acid, 13.51 grams (0.1 mole) of benzoxazolone, and 13.89 g (0.1 mole) of bromoacetic acid. The reaction was heated with stirring at 115° C. for 2.5 hours and poured into 1 kg ice. The mixture was stirred mechanically for 1 hour to form a purple solid, which was then filtered off and washed with water. The solid was slurried with acetone for 30 minutes, a small amount of purple solid filtered off, and the brown filtrate evaporated. The resulting dark brown gum was slurried with 150 ml ethanol for 30 minutes, and the brown solid filtered off and washed with ethanol. This solid had a m.p. of 192°–194° C.

The solid (6.6 grams, 0.0257 mole) was placed in a 100 ml three-necked round-bottomed flask equipped with magnetic stirrer, dropping funnel, thermometer, and nitrogen inlet and 19.15 ml (0.257 mole) of trifluoroacetic acid added. Triethylsilane (9.44 ml, 0.0591 mole) was added dropwise to the stirring slurry over 30 minutes. The reaction was stirred overnight at room temperature, then poured into 150 grams ice. The mixture was stirred for 15 minutes, and the brown gum filtered off. The gum was dissolved in 100 ml ethyl acetate, and 125 ml cyclohexane added, giving a brown precipitate, which was filtered and washed with cyclohexane. The filtrate was evaporated and the resulting yellow solid slurried with 50 ml isopropyl ether the pale yellow solid was filtered off and dried to give 2.7 g 6-(2-bromoethyl)-benzoxazolone (11% yield for two steps), m.p. 148°–151° C.

B. To a 100 ml round-bottomed flask equipped with magnetic stirrer, condenser, and nitrogen inlet were added 0.618 g (2.10 mmol) of N-(1-naphthyl)piperazine 0.472 g (1.95 mmol) of 6-(2-bromoethyl)-benzoxazolone, 0.411 ml (2.92 mmol) of triethylamine, 50 ml ethanol, and a catalytic amount of sodium iodide. The reaction was refluxed for 3 days, cooled, and evaporated to a brown gum. The gum was partitioned between 50 ml water and 75 ml methylene chloride, the pH adjusted with aqueous 1N sodium hydroxide solution, and a little methanol added to facilitate phase separation. The methylene chloride layer was dried over sodium sulfate and evaporated, then chromatographed on silica gel. Fractions containing the product were combined and evaporated, the residue taken up in ethyl acetate, treated with hydrochloride gas, and the resulting hydrochloride salt of the product filtered off to give the white solid title compound, m.p. 282°–285° C., 213 mg (23% yield).

EXAMPLE 2

6-(2-(4-(1-Naphthyl)piperazinyl)ethyl)-benzimidazolone hydrochloride

A. To a 500 ml three-necked round-bottomed flask equipped with mechanical stirrer and nitrogen inlet were added 100 grams of polyphosphoric acid, 6.7 grams (0.05 mole) of benzoxazolone, and 6.95 grams (0.05 mole) of bromoacetic acid. The reaction was heated with stirring at 115° C. for 1.5 hours and poured into 1 kg ice. The mixture was stirred mechanically for 1 hour to form a gray solid, which was then filtered off and washed with water. The solid was slurried with acetone for 30 minutes, a small amount of purple solid filtered off, and the brown filtrate evaporated. The resulting dark brown gum was taken up in ethyl acetate/water, and the organic layer washed with water and brine, dried, and evaporated to solid, 6.5 grams (51%). NMR (δ, DMSO-d$_6$): 5.05 (s, 2H), 7.4 (m, 1H), 7.7–8.05 (m, 2H).

The solid (6.0 grams, 0.0235 mole) was placed in a 100 ml three-necked round-bottomed flask equipped with magnetic stirrer, dropping funnel, thermometer, and nitrogen inlet and 18.2 ml (0.235 mole) of trifluoroacetic acid added. Triethylsilane (8.64 ml, 0.0541 mole) was added dropwise to the stirring slurry over 30 minutes. The reaction was stirred overnight at room temperature, then poured into 150 grams ice. The mixture was stirred for 14 minutes, and the pink solid 6-(2-bromoethyl)-benzimidazolone filtered off to give 5.0 grams (42% yield for two steps), m.p. 226°–230° C.

B. To a 100 ml round-bottomed flask equipped with magnetic stirrer, condenser, and nitrogen inlet were added 2.64 grams (12.4 mmol) of N-(1-naphthyl)-piperazine, 3.0 grams (12.4 mmol) of 6-(2-bromoethyl)-benzimidazolone, 1.31 grams (12.4 mmol) sodium carbonate, 50 ml methylisobutylketone, and a catalytic amount of sodium iodide. The reaction was refluxed for 3 days, cooled, and evaporated to a brown gum. The gum was partitioned between 50 ml water and 75 ml ethyl acetate, and the ethyl acetate layer washed with brine, dried over sodium sulfate, and evaporated, then chromatographed on silica gel. Fractions containing the product were combined and evaporated, the residue taken up in tetrahydrofuran, treated with hydrochloric acid gas, and the resulting hydrochloride salt of the product filtered off to give a white solid, m.p. 260°–262° C., 716 mg (14% yield).

EXAMPLE 3

6-(2-(4-(8-Quinolyl)piperazinyl)ethyl)-benzoxazolone hydrochloride

To a 35 ml round-bottomed flask equipped with condenser and nitrogen inlet were added 0.36 grams (1.5 mmol) of 6-(2-bromoethyl)-benzoxazolone, 0.32 grams (1.5 mmol) of 8-piperazinyl quinoline, 0.2 grams (1.9 mmol) of sodium carbonate, 50 mg of sodium iodide, and 5 ml of ethanol. The reaction was refluxed for 20 hours, cooled, diluted with water, and the pH adjusted to 4 with 1N Sodium hydroxide, and the product extracted into ethyl acetate. The ethyl acetate layer was washed with brine, dried, and evaporated to give 0.3 grams of a yellow oil. The oil was dissolved in ethyl acetate, ethyl acetate saturated with hydrochloric acid gas added, and the mixture concentrated to dryness. The residue was crystallized from isopropanol to give 0.18 grams (32%) of a yellow salt, m.p. >200° NMR ($\delta$, CDCl$_3$): 2.74 (m, 2H), 2.89 (m, 6H), 3.44 (m, 4H), 6.76–7.42 (m, 7H), 8.07 (m, 1H), 8.83 (m, 1H).

EXAMPLE 4

6-(2-(4-(4-Quinazolinyl)piperazinyl)ethyl)-benzoxazolone hydrochloride

To a 35 ml round-bottomed flask equipped with condenser and nitrogen inlet were added 1.22 grams (5.05 mmol) of 6-(2-bromoethyl)benzoxazolone, 1.08 grams (1.5 mmol) of 4-piperazinylquinazoline, 0.85 grams (8.0 mmol) of sodium carbonate, 2 mg of sodium iodide, and 35 ml of ethanol. The reaction was refluxed for 3 days, cooled, diluted with water, and the pH adjusted to 4 with 1N HCl. The aqueous layer was separated, the pH adjusted to 7 with 1N Sodium hydroxide, and the product extracted into ethyl acetate. The ethyl acetate layer was washed with brine, dried, and evaporated to give 1.3 grams of a yellow oil. The oil was crystallized from chloroform (1.1 g), dissolved in ethyl acetate, ethyl acetate saturated with hydrochloric acid gas added, and the mixture concentrated to dryness. The residue gave 0.9 grams (58%) of a yellow salt, m.p. >200° C. NMR ($\delta$, CDCl$_3$): 2.72 (m, 6H), 2.86 (m, 2H), 3.83 (m, 4H), 6.9–7.9 (m, 7H), 8.72 (s, 1H).

EXAMPLE 5

6-(2-(4-(4-Phthalazinyl)piperazinyl)ethyl)-benzoxazolone hydrochloride

To a 35 ml round-bottomed flask equipped with condenser and nitrogen inlet were added 1.13 grams (4.7 mmol) of 6-(2-bromoethyl)-benzoxazolone, 1.0 gram (4.7 mmol) of 4-piperazinyl phthalazine, 0.64 grams (6.0 mmol) of sodium carbonate, and 30 ml of ethanol. The reaction was refluxed for 20 hours, cooled, diluted with water, and the pH adjusted to 4 with 1N HCl. The aqueous layer was separated, the pH adjusted to 7 with 1N Sodium hydroxide, and the product extracted into ethyl acetate. The ethyl acetate layer was washed with brine, dried, and evaporated to give 0.5 grams of a red oil. The oil was chromatographed on silica gel using chloroform/methanol as eluent to give 0.2 grams of a pink oil. The oil was dissolved in ethyl acetate, ethyl acetate saturated with hydrochloric acid gas added and the mixture concentrated to give 0.37 grams (11%) of a yellow salt, m.p. >200° C. NMR ($\delta$, CDCl$_3$): 2.78 (m, 2H), 2.88 (m, 6H), 3.65 (m, 4H), 7.0–8.1 (m, 7H), 9.18 (s, 1H).

EXAMPLE 6

6-(2-(4-(4-Methoxy-1-naphthyl)piperazinyl)ethyl)-benzoxazolone hydrochloride

To a 35 ml round-bottomed flask equipped with condenser and nitrogen inlet were added 0.24 grams (1.0 mmol) of 6-(2-bromoethyl)-benzoxazolone, 0.24 grams (1.0 mmol) of 4-methoxy-1-piperazinyinaphthalene, 0.13 grams (1.2 mmol) of sodium carbonate, and 25 ml of ethanol. The reaction was refluxed for 36 hours, cooled, diluted with water, and the product extracted into ethyl acetate. The ethyl acetate layer was washed with brine, dried, and evaporated to give 0.49 grams of a yellow oil. The oil was chromatographed on silica gel using chloroform as eluent to give 0.36 grams of yellow crystals. The solid was dissolved in ethyl acetate, ethyl acetate saturated with hydrochloric acid gas added, and the mixture concentrated to dryness to give 0.26 grams (55%) of white salt crystals, m.p. >200 °C. NMR ($\delta$, CDCl$_3$): 2.8–3.2 (m, 12H), 4.01 (s, 12H), 6.7–7.6 (m, 7H), 8.26 (m, 2H).

EXAMPLE 7

6-(2-(4-(5-Tetralinyl)piperazinyl)ethyl)-benzoxazolone hydrochloride

To a 35 ml round-bottomed flask equipped with condenser and nitrogen inlet were added 1.0 gram (3.9 mmol) of 6-(2-bromoethyl)-benzoxazolone, 0.85 grams (3.9 mmol) of 5-piperazinyltetralin, 0.4 grams (3.9 mmol) of sodium carbonate, 2 mg of sodium iodide, and 30 ml of isopropanol. The reaction was refluxed for 18 hours, cooled, evaporated to dryness, and the residue dissolved in ethyl acetate/water. The pH was adjusted to 2.0 with 1N HCl, and the precipitate which had formed collected by filtration. The precipitate was suspended in ethyl acetate/water, the pH adjusted to 8.5 with 1N Sodium hydroxide, and the ethyl acetate layer separated. The ethyl acetate layer was washed with brine, dried, and evaporated to give 0.7 grams of a solid. The solid was dissolved in ethyl acetate, ethyl acetate saturated with hydrochloric acid gas added, and the mixture concentrated to dryness to give 0.70 grams (40%) of a yellow salt, m.p. >200° C. NMR ($\delta$, CDCl$_3$): 1.9 (m, 4H), 2.95 (m, 16H), 6.8–7.2 (m, 6H).

EXAMPLE 8

6-(2-(4-(6-Hydroxy-8-quinolyl)piperazinyl)ethyl)-benzoxazolone hydrochloride

To a 35 ml round-bottomed flask equipped with condenser and nitrogen inlet were added 0.84 grams (3.5 mmol) of 6(2-bromoethyl)-benzoxazolone, 0.80 grams (3.5 mmol) of 6-hydroxy-8-piperazinyl quinoline, 0.37 grams (3.5 mmol) of sodium carbonate, 2 mg of sodium iodide, and 30 ml of isopropanol. The reaction was refluxed for 18 hours, cooled, evaporated, and the residue dissolved in ethyl acetate/water. The pH was adjusted to 2.0 with 1N HCl, and the phases separated. The aqueous phase was adjusted to pH 8.5 and extracted with ethyl acetate. The ethyl acetate layer was washed with brine, dried, and evaporated to give 0.33 grams of a yellow solid. The solid was dissolved in ethyl acetate, ethyl acetate saturated with hydrochloric acid gas added, and the mixture concentrated to dryness. The residue was crystallized from isopropanol to give 0.32 grams (20%) of a yellow salt, m.p. 250° C. (dec.). NMR ($\delta$, CDCl$_3$): 2.8 (m, 8H), 3.4 (m, 4H), 6.7–7.3 (m, 7H), 7.7–7.9 (m, 1H).

EXAMPLE 9

6-(2-(4-(1-(6-Fluoro)naphthyl)piperazinyl)ethyl)-benzoxazolone hydrochloride

A. To a round-bottomed flask equipped with condenser and nitrogen inlet were added 345 ml (3.68 mol) of fluorobenzene and 48 grams (0.428 mol) of furoic acid. To the stirring suspension was added in portion 120 grams (0.899 mol) of aluminum chloride. The reaction was then stirred at 95° C. for 16 hours and then quenched by addition to ice/water/1N HCl. After stirring 1 hour, the aqueous layer was decanted off, and benzene and a saturated aqueous solution of sodium bicarbonate added. After stirring 1 hour, the layers were separated, the aqueous layer washed with benzene, acidified, and extracted into ethyl acetate. The ethyl acetate layer was washed with water and brine, dried over sodium sulfate, and evaporated to a solid. The solid was triturated with isopropyl ether to give 5.0 grams (6.1%) of white solid 6-fluoro-1-naphthoic acid, NMR ($\delta$, DMSO-$d_6$): 7.0–8.0 (m, 5H), 8.6 (m, 1H).

B. To a 125 ml round-bottomed flask equipped with condenser, addition funnel, and nitrogen inlet were added 5.0 grams (26.3 mmol) of 6-fluoro-1-naphthoic acid and 50 ml acetone. To the stirring suspension were added dropwise 6.25 ml (28.9 mmol) of diphenyl phosphoryl azide and 4 ml (28.9 mmol) of triethylamine. The reaction was refluxed 1 hour, poured into water/ethyl acetate, and filtered. The filtrate was washed with water and brine, dried over sodium sulfate, and evaporated. The residue was further treated with hydrochloric acid to form the hydrochloride salt and then liberated with sodium hydroxide to afford the free base 6-fluoro-1-amino-naphthalene as an oil, 1.0 gram (24%).

C. To a 125 ml round-bottomed flask equipped with condenser and nitrogen inlet were added 1.0 gram (6.21 mmol) of 6-fluoro-1-amino-naphthalene, 1.8 grams (7.76 mmol) of N-benzyl bis(2-chloroethyl)amine hydrochloride, 3.3 ml (19.2 mmol) of diisopropylethylamine, and 50 ml isopropanol. The reaction was refluxed 24 hours, cooled, and evaporated to an oil. The oil was taken up in ethyl acetate, washed with water and brine, dried over sodium sulfate, and evaporated to an oil. The oil was chromatographed on silica gel using methylene chloride as eluent to afford 1.5 grams (75.5%) of an oil, 1-benzyl-4-(6-fluoronaphthyl)-piperazine.

D. To a 125 ml round-bottomed flask equipped with nitrogen inlet were added 1.5 grams (4.69 mmol) of 1-benzyl-4-(6-fluoronaphthyl)-piperazine, 1.2 ml (31.3 mmol) of formic acid, 3.0 grams 5% palladium on carbon, 50 ml ethanol. The reaction was stirred at room temperature for 16 hours, the catalyst filtered under $N_2$, and the solvent evaporated. The oil, N-(1-(6-fluoro)naphthyl)-piperazine (0.420 grams, 39%), was used directly in the following step.

E. To a 100 ml round-bottomed flask equipped with magnetic stirrer, condenser, and nitrogen inlet were added 0.420 grams (1.83 mmol) of N-(6-fluoro-1-naphthyl) piperazine, 0.440 grams (1.83 mmol) of 6-(2-bromoethyl)-benzoxazolone, 194 mg (1.83 mmol) of sodium carbonate, 50 ml methylisobutylketone, and a catalytic amount of sodium iodide. The reaction was refluxed for 3 days, cooled, and evaporated to a brown gum. The gum was partitioned between 50 ml water and 75 ml ethyl acetate, the pH adjusted with aqueous 1N Sodium hydroxide solution, the layers separated, and the ethyl acetate layer washed with water and brine. The ethyl acetate layer was dried over sodium sulphate and evaporated, and the residue was then chromatographed on silica gel. Fractions containing the product were combined and evaporated, the residue taken up in ether/methylene chloride, treated with hydrochloric acid gas, and the resulting hydrochloride salt of the product filtered off to give a white solid, m.p. 295°–300° C., 214 mg (22% yield).

EXAMPLE 10

6-(4-(4-(1-Naphthyl)piperazinyl)butyl)-benzoxazolone hydrochloride

A. To a 500 ml round-bottomed flask equipped with mechanical stirrer and nitrogen inlet were added 200 grams polyphosphoric acid, 16.7 grams (0.1 mol) 4-bromobutyric acid, and 13.51 grams (0.1 mol) benzoxazolone. The reaction was heated at 115° C. for 1 hour and 60° C. for 1.5 hours. It was then poured onto ice, stirred for 45 minutes and the solid filtered and washed with water. The solid was suspended in acetone, stirred for 20 minutes, filtered, washed with petroleum ether, and dried to give 12.3 grams (43%) of white solid 6-(4-bromobutyryl)-benzoxazolone NMR ($\delta$, DMSO-$d_6$): 1.77 quin, 2H), 3.00 (t, 2H), 3.45 (t, 2H), 7.0–7.8 (m, 3H).

B. To a 100 ml three-necked round-bottomed flask equipped with dropping funnel, thermometer, and nitrogen inlet were added 10 grams (0.035 mol) 6-(4-bromobutyryl)-benzoxazolone and 26.08 ml (0.35 mol) trifluoroacetic acid. To the stirring suspension was added dropwise 12.93 ml (0.080 mol) triethylsilane, and the reaction stirred at room temperature for 16 hours. The reaction was then poured into water, and the resulting white solid filtered and washed with water. It was then suspended in isopropyl ether, stirred, and filtered to afford white solid 6-(4-trifluoroacetoxybutyl)-benzoxazolone, m.p. 100°–103° C., 10.47 grams (98.7%).

C. To a 250 ml round-bottomed flask equipped with nitrogen inlet were added 5.0 grams (0.0164 mol) 6-(trifluoroacetoxybutyl)-benzoxazolone, 100 ml methanol, and 1 gram sodium carbonate. The reaction was stirred at room temperature for 1 hour, evaporated, and the residue taken up in methylene chloride/methanol, washed with aqueous HCl, dried over sodium sulfate, and evaporated to white solid 6-(4-chlorobutyl)-benzoxazolone, m.p. 130°–133° C., 2.57 grams (75.7%).

E. To a 100 ml round-bottom flask equipped with condenser and nitrogen inlet were added 0.658 grams (3.10 mmol) of 6-(4-chlorobutyl)-benzoxazolone, 0.7 grams (3.10 mmol) of N-(1-naphthyl)piperazine, 0.328 grams sodium carbonate, 2 mg sodium iodide, and 50 ml isopropanol. The reaction was refluxed for 3 days, evaporated, taken up in methylene chloride, washed with water, dried over sodium sulfate, and evaporated. The residue was chromatographed on silica gel using ethyl acetate as eluent, and the product dissolved in acetone, precipitated with ethereal HCl, and the white solid filtered, washed with acetone, and dried to afford 6.76 grams (46.0%) of a white solid, m.p. 231°–233° C.

EXAMPLE 11

6-(2-(4-(N-(3-Trifluoromethyl)phenylindazolyl)-piperazinyl)ethyl)benzoxazolone hydrochloride To a 125 ml round-bottomed flask equipped with condenser were added 1.0 gram (2.89 mmol) of N-(3-trifluoromethylphenyl)indazolyl)piperazine, 0.70 grams (2.89 mol) of 6-(2-bromoethyl)benzoxazolone, 0.31 grams (2.89 mmol) of sodium carbonate, and 50 ml of methyl isobutyl ketone, and the mixture refluxed 18 hours. The reaction was cooled and partitioned between ethyl acetate and water. The ethyl acetate layer was isolated, washed with water and saturated aqueous sodium chloride solution, dried over sodium sulfate, and evaporated to an oil. The oil was chromatographed on silica gel using ethyl acetate/methylene chloride as eluent, and the product fractions collection and dissolved in ether, precipitated with hydrochloride gas, and the solid collected to give the hydrochloride salt of the title compound, m.p. 280°–282° C., 0.75 grams (47%).

EXAMPLE 12

5-(2-(4-(1-Naphthyl)piperazinyl)ethyl)oxindole hydrochloride

A. To a 250 ml round-bottomed flask equipped with condenser and nitrogen inlet were added 30.7 grams (230 mmol) aluminum chloride, 150 ml carbon disulfide, and 3.8 ml (48 mmol) chloroacetyl chloride. To the stirring mixture was added 5.0 grams (37 mmol) of oxindole portionwise over 15 minutes. The reaction was stirred a further 10 minutes, then refluxed 2 hours. The reaction was cooled, added to ice, stirred thoroughly, and the beige precipitate filtered, washed with water, and dried to afford 7.67 grams (97%) of 5-chloroacetyl-oxindole. NMR ($\delta$, DMSO-$d_6$): 3.40 (s, 2H), 5.05 (s, 2H), 6.8–7.9 (m, 3H).

B. To a 100 ml round-bottomed flask equipped with condenser and nitrogen inlet were added 5.0 grams (23.9 mmol) of 5-chloroacetyl oxindole and 18.5 ml triflouroacetic acid. To the stirring solution was added 8.77 ml (54.9 mmol) of triethylsilane while cooling to prevent exotherm, and the reaction stirred 16 hours at room temperature. The reaction was then poured into ice water, stirred and the beige solid filtered, washed with water and hexane, and dried to give 5-(2-chloroethyl)oxindole, m.p. 168°–170° C., 3.0 grams (64%).

C. To a 50 ml round bottomed flask equipped with condenser and nitrogen inlet were added 370 mg (1.69 mmol) 5-(2-chloroethyl)oxindole, 400 mg (1.69 mmol) N-(1-naphthyl)piperazine hydrochloride, 200 mg (1.69 mmol) sodium carbonate, 2 mg sodium iodide, and 50 ml methylisobutylketone. The reaction was refluxed 24 hours, cooled, and evaporated. The residue was taken up in ethyl acetate, washed with water and brine, dried over sodium sulfate, and evaporated. The residue was chromatographed on silica gel with ethyl acetate, and the product fractions collected and evaporated to give a foam. The foam was dissolved in ether, treated with hydrochloric acid gas, and the precipitate collected, washed with ether, and dried to afford a white solid, m.p. 303°–305° C., 603 mg (84%).

EXAMPLE 13

6-(2-(4-(4-(2,1,3-Benzothiadiazolyl)piperazinyl) ethyl)-benzoxazolone hydrochloride A. To a 125 ml round-bottomed flask equipped with condenser and nitrogen inlet were added 2.0 grams (13.2 mmol) 4-amino-2,1,3-benzothiadiazole, 2.54 grams (13.2 mmol) mechlorethamine hydrochloride, 4.19 grams (39.6 mmol) sodium carbonate, 2 mg sodium iodide, and 50 ml ethanol. The reaction was refluxed 2 days, cooled, and evaporated. The residue was taken up in methylene chloride, washed in water, dried over sodium sulfate, and evaporated. The residue was chromatographed on silica gel using ethyl acetate/methanol as eluent, and the product fractions collected and evaporated to an oil of 4-(2,1,3-benzothiadiazolyl)-N-methylpiperazine, 628 mg (20%). NMR ($\delta$, CDCl$_3$): 2.5 (s, 3H), 2.8 (m, 4H), 3.6 (m, 4H), 6.8 (m, 1H), 7.5 (m, 2H).

B. To a 25 ml round-bottomed flask equipped with condenser and nitrogen inlet were added 620 mg (2.64 mmol) of 4-(2,1,3-benzothiadiazolyl)-N-methylpiperazine, 0.224 ml (2.64 mmol) vinyl chloroformate, and 15 ml dichloroethane. The reaction was refluxed 16 hours, cooled, and evaporated. The residue was chromatographed on silica gel using methylene chloride/ethyl acetate as eluent, and the product fractions collected to give yellow solid 4-(2,1,3-benzothiadiazolyl)-N-vinyloxycarbonylpiperazine, 530 mg (69%). NMR ($\delta$, CDCl$_3$): 3.6 (m, 4H), 3.8 (m, 4H). 4.4–5.0 (m, 2H), 6.6–7.6 (m, 4H).

C. To a 50 ml round-bottomed flask equipped with condenser and nitrogen inlet were added 530 mg (1.83 mmol) 4-(2,1,3-benzothiadiazolyl)-N-vinyloxycarbonylpiperazine and 25 ml ethanol, and the suspension saturated with hydrochloric acid gas. The reaction was refluxed 2.75 hours, cooled and evaporated. The residue was triturated with acetone to give a yellow solid N-(2,1,3-benzothiadiazolyl)-piperazine, m.p. 240°–244° C., 365 mg (62%).

D. To a 125 ml round-bottomed flask equipped with condenser and nitrogen inlet were added 365 mg (1.13 mmol) N-(2,1,3-benzothiadiazolyl)-piperazine, 275 mg (1.13 mmol) 6-(2-bromoethyl)benzoxazolone, 359 mg (3.39 mmol) sodium carbonate, 2 mg sodium iodide and 40 ml ethanol. The reaction was heated at reflux for 2 days, cooled and evaporated. The residue was taken up in methylene chloride, washed with water, dried over sodium sulfate, and evaporated. The residue was chromatographed on silica gel using ethyl acetate/methanol as eluent and the product fractions collected, dissolved in methylene chloride/ methanol, precipitated by addition of and ethereal solution of HCl, and the solid filtered, washed with ether, and dried to give 228 mg (45%), m.p. 166°–170° C.

EXAMPLE 14

6-(2-(4-(1-Naphthyl)-piperazinyl)ethyl) benzothiazolone

To a 100 ml round-bottomed flask with condenser and nitrogen inlet were added 1.0 gram (3.88 mmol) of 6-(2-bromoethyl)benzothiazolone, 822 mg (3.88 mmol) N-(1-naphthyl)piperazine, 410 mg (3.88 mmol) sodium carbonate, and 50 ml methylisobutlyketone. The reaction was refluxed for 24 hours, cooled, and evaporated. The residue was taken up in ethyl acetate, washed with water and brine, dried over sodium sulfate, and evaporated. The resulting solid was treated with hot ethyl acetate to afford a white solid, m.p. 198°–220° C., 540 mg (36%).

EXAMPLE 15

6-(2-(4-(3-benzisothiazolyl)piperazinyl)ethyl) benzoxazolone

To a 125 ml round-bottomed flask equipped with condenser were added 4.82 grams (0.022 mol) of N-(3-benzisothiazolyl)piperazine (prepared according to the procedure given in U.S. Pat. No. 4,411,901), 5.32 grams (0.022 mol) of 6-(2-bromoethyl)benzoxazolone, 2.33 grams (0.022 mol) of sodium carbonate, and 50 ml of methyl isobutyl ketone. The mixture was refluxed for 18 hours. The reaction was cooled and partitioned between ethyl acetate and water. The ethyl acetate layer was isolated, washed with water and saturated aqueous sodium chloride solution dried over sodium sulfate, and evaporated to an oil. The oil was chromatographed on silica gel using ethyl acetate as eluent, and the product fractions collected, concentrated to dryness and triturated with methylene chloride/isopropyl ether to give a white solid, 1 m.p. 185°–187° C. NMR ($\delta$, CDCl$_3$): 1.7 (bs, 1H), 2.8 (m, 8H), 3.6 (m, 4H), 6.9–8.0 (m, 7H).

EXAMPLE 16

5-(2-(4-(1,2-benzisothiazol-3-yl)-piperazinyl)ethyl) oxindole hydrochloride

To a 125 ml round-bottom flask equipped with nitrogen inlet and condenser were added 0.70 grams (3.20mmol) N-(3-benzisothiazolyl)-piperazine, 0.62 grams (3.20 mmol) 5-(2-chloroethyl)-oxindole, 0.68 grams (6.40 mmol) sodium carbonate, 2 mg sodium iodide, and 30 ml methylisobutyl ketone. The reaction was refluxed 40 hours, cooled, filtered, and evaporated. The residue was chromatographed on silica gel, eluting the byproducts with ethyl acetate (1:1) and the product with 4% methanol in ethyl acetate (1.5:1). The product fractions ($R_f$=0.2 in 5% methanol in ethyl acetate) were evaporated, taken up in methylene chloride, and precipitated by addition of ether saturated with HCl; the solid was filtered and washed with ether, dried, and washed with acetone. The latter was done by slurrying the solid acetone and filtering. The title compound was obtained as a high melting, non-hygroscopic solid product, m.p. 288°–288.5° C., 0.78 (59%).

In a manner analogous to that for preparing 5-(2-(4-(1,2-benzisothiazol-3-yl)piperazinyl)ethyl)-oxindole, the following compounds were made:

5-(2-(4-(1,2-benzisothiazol-3-yl)piperazinyl)ethyl)-1-ethyloxindole hydrochloride, 25%, m.p. 278°–279° C.;

5-(2-(4-(1,2-benzisothiazol-3-yl)piperazinyl)ethyl)-1-methyloxindolehydrochloride hemihydrate, 42%, m.p. 283°–285° C.; MS(%): 392(1), 232(100), 177(31); Anal. for $C_{22}H_{24}N_4OS \cdot HCl \cdot \frac{1}{2}H_2O$: C 60.33, H 5.98, N 12.79. Found: C 60.37, H 5.84, N 12.77;

5-(2-(4-(1,2-benzisothiazol-3-yl)piperazinyl)ethyl)-1-(3-chlorophenyl)oxindole hydrochloride hydrate, 8%, m.p. 221°–223° C.; MS(%): 488(1), 256(4), 232(100), 177(15) Anal. for $C_{27}H_{25}ClN_4OS \cdot HCl \cdot H_2O$: C 59.67, H 5.19, N 10.31. Found: C 59.95, H 5.01, N 10.14;

5-(2-(4-(1,2-benzisothiazol-3-yl)piperazinyl)ethyl)-3,3-dimethyloxindole hydrochloride hemihydrate, 40%, m.p. 289°–291° C.; MS(%): 406(1), 232(100), 177(42); Anal. for $C_{23}H_{26}N_4,OS \cdot HCl \cdot \frac{1}{2}H_2O$: C 61.11, H 6.24, 12.39. Found: C 61.44, H 6.22, N 12.01;

5-(2-(4-(1,2-benzisothiazol-3-yl)piperazinyl)ethyl)-1,3-dimethyloxindole, 76%, m.p. 256° C.;

5'-(2-(4-(1,2-benzisothiazol-3-yl)piperazinyl)ethyl)-spiro[cyclopentane-1,3'-indoline-]-2'-one hydrochloride hemihydrate, 50%, m.p. 291°–293° C. (dec.); MS(%): 432(1) 232(100), 200(11), 177(36); Anal. for $C_{25}H_{28}N_4OS \cdot HCl \cdot \frac{1}{2}H_2O$: C 62.81, H 6.33, N 11.72. Found: C35 11.34;

5-(2-(4-(1,2-benzisothiazol-3-yl)piperazinyl)ethyl)-1,3,3-trimethyloxin dole hydrochloride hemihydrate, 63%, m.p. 225°–257° C.; MS(%): 420(1), 232(100), 177(37); Anal. for $C_{24}H_{28}N_4OS \cdot HCl \cdot \frac{1}{2}H_2O$: C 61.85, H 6.49, N 12.02. Found: C 61.97, H 6.34;

5-(2-(4-(1,2-benzisothiazol-3-yl)piperazinyl)ether)-6-fluorooxindole hydrochloride hydrate, 18%, m.p. 291°–293° C.; MS(%): 396(1), 232(100), 177(53); Anal. for $C_{21}H_{21}H_4FOS \cdot HCl \cdot \frac{1}{2}H_2O$: C 55.93, H 5.36, N 12.42. Found: C 56.39, H 5.30, N 12,19;

5-(2-(4-(1,2-benzisothiazol-3-yl)piperazinyl)ethyl)-7-fluorooxindole hydrochloride, 9%, m.p. 253° C.;

5-(2-(4-(1,2-benzisothiazol-3-yl)piperazinyl)ethyl)-6-chlorooxindole hydrochloride, 20%, m.p. >300° C.; MS(%): 488(1), 256(4), 232(100), 177(15); Analysis for $C_{21}H_{21}ClN_4OS \cdot HCl \cdot \frac{1}{2}H_2O$:
C 52.50, H 4.71, N 11.39. Found: C 52.83, H 4.93, N 11.42;

5-(2-(4-(1,2-benzisothiazol-3-yl)piperazinyl)ethyl)-6-fluoro-3,3-dimethyloxindole hydrochloride, 35%, m.p. 284°–286° C.; Anal. for $C_{23}H_{25}FN_4OS \cdot HCl \cdot H_2O$: C 57.67, H 5.89, N 11.70. Found: C 58.03, H 5.79, N 11.77;

5-(2-(4-(1,2-benzisothiazol-3-yl)piperazinyl)butyl)oxindole hemihydrate, 26%, m.p. 131°–135° C.;

MS(%): 406(2), 270(8), 243(65), 232(23), 177(45), 163(100) Anal. for $C_{23}H_{26}N_4OS \cdot \frac{1}{2}H_2O$: C 66.48, H 6.55, N 13.48. Found: C 66.83, H 6.30, N 13.08;

5-(2-(4-(1,2-benzisothiazol-3-yl)piperazinyl)butyl)-7-fluorooxindole hydrate, 7%, m.p. 126°–129° C.; MS(%): 424(3); Anal. for $C_{23}H_{25}FN_4OS \cdot H_2O$: C 57.67, H 5.89, N 11.70. Found: C 57.96, H 5.62, N 11.47;

5-(2-(4-(1,2-benzisothiazol-3-yl)piperazinyl)butyl)-1-ethyloxindole hemihydrate, 25%, m.p. 126°–128° C.; MS(%): 434(2), 298(10), 271(55), 232(34), 177(53), 163(100); Anal. for $C_{25}H_{30}N_4OS \cdot \frac{1}{2}H_2O$: C 67.69, H 7.04, N 12.63. Found: C 67.94, H 6.73, N 12.21;

5-(2-(4-(naphthalen-1-yl)piperazinyl)ethyl)-1-ethyloxindole hydrochloride hydrate, 21%, m.p. >300°C.; MS(%): 399(1), 225(96), 182(30), 70(100); Anal. for $C_{26}H_{29}N_3O \cdot HCl \cdot H_2O$: C 68.78, H 7.10, N 9.26. Found: C 69.09, H 6.72, N 9.20;

5-(2-(4-(naphthalen-1-yl)piperazinyl)ethyl)-6-fluorooxindole hydrochloride, 23%, m.p. 289°–291° C.; MS(%): 389(1), 232(3), 225(100), 182(32), 70(84); Anal. for $C_{24}H_{24}FN_3O \cdot HCl \cdot \frac{1}{2}CH_2Cl_2$; C 62.82, H 5.60, N 8.97. Found: C 62.42, H 5.82, N 8.77;

5-(2-(4-(naphthalen-1-yl)piperazinyl)ethyl)-7-fluorooxindole hydrochloride, 22%, m.p. 308° C.(dec.); MS(%): 389(1), 225(100); Anal. for $C_{24}H_{24}FN_3O \cdot HCl \cdot CH_2Cl_2$; C 58.78, H 5.93, N 8.23. Found: C 58.82, H 5.80, N 8.27;

EXAMPLE 17

6-(4-(2-(3-Benzisothiazolyl)piperazinyl)ethyl) benzothiazolone hydrochloride

To a 100 ml round-bottomed flask equipped with condenser and nitrogen inlet were added 1.03 grams (4 mmol) 6-(2-bromoethyl)-benzothiazolone, 0.88 grams (4 mmol) N-(3-benzisothiazolyl)-piperazine, 0.84 grams (8 mmol) sodium carbonate, 2 mg sodium iodide, and 40 ml methylisobutyl ketone. The reaction was refluxed 36 hours, cooled, filtered, and the filtrate evaporated. The residue was chromatographed on silica gel using ethyl acetate as eluent to afford an oil, which was taken up in methylene chloride and precipitated by addition of ether saturated with HCl. The solid was filtered, washed with ether, dried briefly, washed with a minimal amount of acetone and dried to afford a white solid, m.p. 288°–2900° C., 1.44 grams (76.7%).

PREPARATION A

A. Following the general procedure for the preparation of 5-(chloroacetyl)oxindole in Example 12A, the following intermediates were prepared from the appropriate oxindoles:

5-(chloroacetyl)-1-ethyl-oxindole, 81%, m.p. 157°–159° C., NMR(CDCl$_3$); δ1.30(t,3H), 3.60(s,2H), 3.85(q,2H), 4.70(s,2H), 6.85–8.15(m,2H);

5-(chloroacetyl)-1-methyloxindole, $C_{11}H_{10}ClNO_2$, 92%, m.p. 201°–202° C.;

1-(3-chlorophenyl)-5(chloroacetyl)oxindole, 98% m.p. 143°–145° C., NMR(DMSO-d$_6$): δ 3.85(br s,2H), 5.10 (s,2H), 6.8(d,1H), 7.4–7.6(m,4H), 7.9 (s+d,2H); MS(%): 319(17, 270(100), 179(46), 178(38);

1,3-dimethyl-5-(chloroacetyl)oxindole, 97% m.p. 206°–207° C.

5-(chloroacetyl)-spirocyclopentane[1,3']-indol-2'-one, 99%, m.p. 203°–204° C.(dec.);
NMR(DMSO-d$_6$): δ 2.0(br s,8H), 4.95(s,2H), 6.9(d,1H), 7.8(d+s,2H), 10.6(br s, 1H);

5-(chloroacetyl)-1,3,3-trimethyloxindole, 82%, m.p. 182°–185° C., NMR(CDCl$_3$): δ 1.45(s,6H), 3.25(s,3H), 4.65(s,2H), 6.9(d,1H), 7.9(s,1H), 8.0(d,1H);

6-fluoro-5-(chloroacetyl)oxindole, 96%, m.p. 178°–180° C.; NMR(DMSO-d$_6$): δ 3.5(s,2H), 4.8(d,2H), 6.7–7–2 (m,2H), 7.8(d,1H);

7-fluoro 5-(chloroacetyl)oxindole, 91%, m.p. 194°–196° C., NMR(DMSO-d$_6$): δ 3.68(s,2H), 5.13(s,2H) 7.65–7.9(dd,2H);

6-chloro-5-(chloroacetyl)oxindole, 99%, m.p. 206°–207° C.;

5-(chloroacetyl)-3,3-dimethyl-6-fluorooxindole, 89%, m.p. 185°–188° C.;

5-(4-chlorobutyryl)oxindole, 84%, oil, MS(%): 239, 237 (55);

1-ethyl-5-(4-chlorobutyryl)oxindole, 99%, oil, NMR (CDCl$_3$): δ 1.2(t,3H), 1.5–2.7(m,5H), 3.0–3.2(m,2H), 3.5–4.0(m,3H), 6.8–7.0(d,1H), 7.9(s,1H), 7.95(d,1H) and 5-(y-chlorobutyryl)-7-fluorooxindole, 53%, m.p. 156°–160° C.

PREPARATION B

By the same procedure as that used to prepare 5-(2-chlorethyl)oxindole in Example 12B, the following were prepared:

5-(2-chloroethyl)-1-ethyloxindole, 93%, m.p. 120°–122° C.; NMR (CDCl$_3$): δ 1.30(t,2H), 3.55(s,2H), 3.654.0 (m,4H), 6.8–7.3(m,3H);

5-(2-chloroethyl)-1-methyloxindole, 99%, m.p. 127°–130° C.; NMR (CDCl3): δ 3.1(t,2H), 3.2(s,2H), 3.5(s,2H), 3.75(t,2H), 6.8(d,1H), 7.15(s,1H), 7.3(d, 1H);

5-(2-chloroethyl)-1-(3-chlorophenyl)oxindole, 83%, m.p. 75°–76° C.;

5-(2-chloroethyl)-1,3-dimethyloxindole, 58%, m.p. 73°–75° C., NMR CDCl$_3$): δ 1.45–1.55(d,3H), 3.03–3.2(t,2H), 3.25(s,3H), 3.30–3.60(q,1H), 3.65–3.90(t,2H), 6.85–6.90(d,1H), 7.15(s,1H), 7.15–7.30(d,1H);

5'-(2-chloroethyl)-spiro[cyclopentane-1,3'-indoline]-2'-one, 92%, m.p. 140°–142° C.; NMR(DMSO-d$_6$): δ 2.8(br s,8H), 2.90(t,2H), 3.7(t,2H), 6.6–7.1(m,3H), 10.2(br s,1H);

5-(2-chloroethyl)-,3,3-trimethyloxindole, 83%, oil;

5-(2-chloroethyl)-6-fluorooxindole 62%, m.p. 188°–190° C.; NMR(DMSO-d$_6$) δ 3.05(t,2H),3.5(2,2H), 3.85(t, 2H), 6.6–7.3(m,2H);

5-(2-chloroethyl)-7-fluorooxindole, 79%, m.p. 176°–179° C.; MS(%); 213(50), 180(20), 164(100), 136(76);

5-(2-chloroethyl)-6-chlorooxindole, 94%, m.p. 210°–211° C.;

5-(2-chloroethyl)-3,3-dimethyl-6-fluorooxindole (C$_{12}$H$_{13}$ClFNO, 84%, m.p. 195°–196° C. NMR (DMSO-d$_6$): δ 1.3(s,6H), 3.05(t,2H), 3.7(t,2H), 6.65(d, 1H), 7.1(d,1H), 10.1(br s, 1H);

5-(4-chlorobutyl)oxindole, 40%, oil, NMR(CDCl$_3$): δ 1.6–2.0(m,4H), 2.6(m,2H), 3.6(m,4H), 6.8–7.15(m, 3H), 9.05(br s, 1H);

5-(4-chlorobutyl)-1-ethyloxindole, 48%, oil, NMR (CDCl$_3$): δ 1.25(t,3H), 1.5–1.95(m,4H), 2.6(m,2H), 3.5(s,2H), 3.55(t,2H), 3.75(q,2H), 6.7–7.2(m,3H); and 5-(4-chlorobutyl)-7-fluorooxindole, 71%, m.p. 168°–173° C.

What is claimed is:

1. A method for treating a condition or disorder that can be treated by decreasing intraocular pressure in a mammal, comprising administering to said mammal a therapeutically effective amount of a compound of the formula

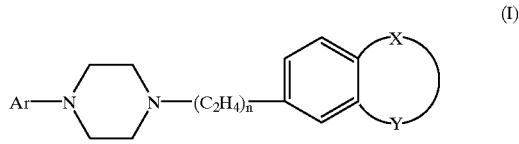

(I)

or a pharmaceutically acceptable acid addition salt thereof, wherein

Ar is benzoisothiazolyl or an oxide or dioxide thereof each optionally substituted by one fluoro, chloro, trifluoromethyl, methoxy, cyano or nitro; naphthyl optionally substituted by fluoro, chloro, trifluoromethyl, methoxy, cyano or nitro; quinolyl; 6-hydroxy-8-quinolyl; isoquinolyl; quinazolyl; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; or phthalazinyl;

n is 1 or 2; and

X and Y together with the phenyl to which they are attached form a cyclic ring system selected from quinolyl; 2-hydroxyquinolyl; benzothiazolyl; 2-aminobenzothiazolyl; benzoisothiazolyl; indazolyl; 2-hydroxyindazolyl; indolyl; oxindolyl optionally substituted by spirocycloalkyl wherein said cycloalkyl moiety contains from 4 to 7 carbon atoms, or by one to three of (C$_1$–C$_3$)alkyl, or by one of chloro, fluoro or phenyl wherein said phenyl is optionally substituted by one chloro or fluoro; benzoxazolyl; 2-aminobenzoxazolyl; benzoxazolonyl; 2-aminobenzoxazolinyl; benzothiazolonyl; benzoimidazolonyl; and benzotriazolyl.

2. A method for treating glaucoma or ischemic retinopathy in a mammal, comprising administering to said mammal a pharmaceutically effective amount of a compound of the formula

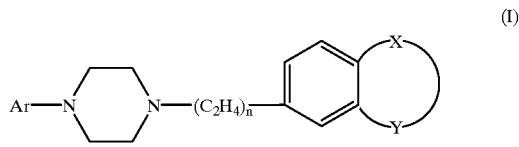

(I)

or a pharmaceutically acceptable acid addition salt thereof, wherein

Ar is benzoisothiazolyl or an oxide or dioxide thereof each optionally substituted by one fluoro, chloro, trifluoromethyl, methoxy, cyano or nitro; naphthyl optionally substituted by fluoro, chloro, trifluoromethyl, methoxy, cyano or nitro; quinolyl; 6-hydroxy-8-quinolyl; isoquinolyl; quinazolyl; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; or phthalazinyl;

n is 1 or 2; and

X and Y together with the phenyl to which they are attached form a cyclic ring system selected from quinolyl; 2-hydroxyquinolyl; benzothiazolyl; 2-aminobenzothiazolyl; benzoisothiazolyl; indazolyl; 2-hydroxyindazolyl; indolyl; oxindolyl optionally substituted by spirocycloalkyl wherein said cycloalkyl moiety contains from 4 to 7 carbon atoms, or by one to three of $(C_1-C_3)$alkyl, or by one of chloro, fluoro or phenyl wherein said phenyl is optionally substituted by one chloro or fluoro; benzoxazolyl; 2-aminobenzoxazolyl; benzoxazolonyl; 2-aminobenzoxazolinyl; benzothiazolonyl; benzoimidazolonyl; and benzotriazolyl.

3. A method according to claim 2, wherein said method is for the treatment of glaucoma.

4. A method according to claim 2, wherein said method is for the treatment of ischemic retinopathy.

5. A method according to claim 2, wherein the compound or pharmaceutically acceptable salt that is adminstered is one wherein X and Y, together with the phenyl to which they are attached, form a benzoxazolonyl group.

6. A method according to claim 2, wherein the compound or pharmaceutically acceptable salt that is administered is one wherein Ar is benzoisothiazolyl and n is 1.

7. A method according to claim 2, wherein the compound or pharmaceutically acceptable salt that is administered is one wherein X and Y, together with the phenyl to which they are attached, form an oxindole that is optionally substituted by chloro, fluoro or phenyl.

8. A method according to claim 2, wherein the compound or pharmaceutically acceptable salt that is adminstered is one wherein Ar is naphthyl and n is 1.

9. A method according to claim 2, wherein the compound or pharmaceutically acceptable salt that is administered is ziprasidone or a pharmaceutically acceptable salt of ziprasidone.

10. A method according to claim 2, wherein the compound or pharmaceutically acceptable salt that is administered is ziprasidone mesylate trihydrate or ziprasidone hydrochloride monohydrate.

* * * * *